(12) United States Patent
Burns et al.

(10) Patent No.: US 6,919,483 B2
(45) Date of Patent: Jul. 19, 2005

(54) IMMUNOMODULATION WITH NOVEL PHARMACEUTICAL COMPOSITIONS

(75) Inventors: Mark R. Burns, Shoreline, MA (US);
Maralee McVean, Seattle, WA (US);
Kevin J. Kennedy, Seattle, WA (US);
Arthur Yeung, Bellevue, WA (US);
Bruce H. Devens, St. Louis, MO (US)

(73) Assignee: Mediquest Therapeutics, Inc., Bothell, WA (US)

( * ) Notice: Subject to any disclaimer, the term of this patent is extended or adjusted under 35 U.S.C. 154(b) by 37 days.

(21) Appl. No.: 10/443,743

(22) Filed: May 23, 2003

(65) Prior Publication Data

US 2004/0235960 A1 Nov. 25, 2004

(51) Int. Cl.[7] .................... C07C 211/13; A61K 31/13; A61K 31/40; A61K 31/445
(52) U.S. Cl. .................. 564/453; 564/454; 564/461; 564/511; 564/512; 548/557; 548/558; 546/244; 514/315; 514/329; 514/426; 514/673; 514/674
(58) Field of Search .................. 564/453, 454, 564/461, 511, 512; 548/557, 558; 546/244; 514/673, 674, 315, 329, 426

(56) References Cited

U.S. PATENT DOCUMENTS 4,507,321 A * 3/1985 Raisfeld .............. 514/673

OTHER PUBLICATIONS

The Merck Index, 12th ed. (1996), Merck & Co., Inc., Whitehouse Station, NJ, p. 8899 entry No. 8894.*

* cited by examiner

*Primary Examiner*—Brian Davis
(74) *Attorney, Agent, or Firm*—Connolly, Bove, Lodge & Hutz, LLP

(57) ABSTRACT

The synthesis and use of a novel class of tumor necrosis factor (TNFα) inhibitors and immunomodulators are provided. These compounds have pharmacological applications as well as uses in assays relating to TNFα and other involved cytokines. As pharmaceuticals, these compounds are used to treat inflammatory, infectious, autoimmune or other proliferative diseases and conditions related to the unwanted presence or activity of TNFα and/or one or more other involved cytokines, alone or in combination with other agents. Examples of compounds of the present invention are those having the structures as shown below:

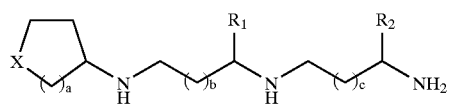

wherein, a, b and c may be the same or different and are integers from 0 to 12, X equals NH or CHNH$_2$, R$_1$ and R$_2$ can be the same or different and equal to a hydrogen or a straight or branched C$_1$ to C$_{20}$ saturated or unsaturated aliphatic; aliphatic amine; an alicyclic; single or multi-ring aromatic; a single or multi-ring aromatic heterocycle; a single or multi-ring saturated heterocycle and the halogenated forms thereof; and

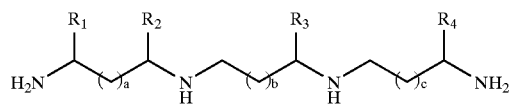

wherein, a, b and c may be the same or different and are integers from 0 to 12; R$_1$, R$_2$, R$_3$, and R$_4$ can be the same or different and equal to a hydrogen or a straight or branched C$_1$ to C$_{20}$ saturated or unsaturated aliphatic; aliphatic amine; an alicyclic; single or multi-ring aromatic; a single or multi-ring aromatic heterocycle; a single or multi-ring saturated heterocycle and the halogenated forms thereof.

18 Claims, 21 Drawing Sheets

Fig. 1
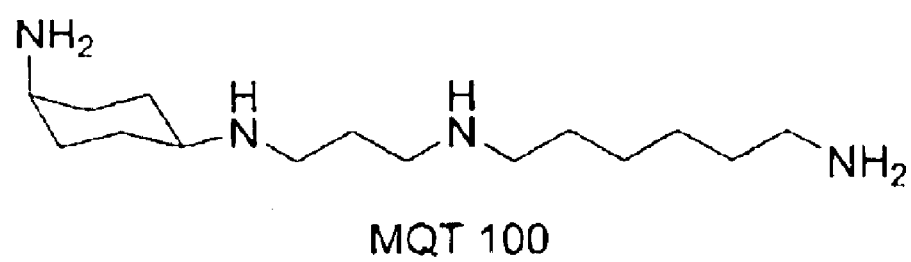
MQT 100
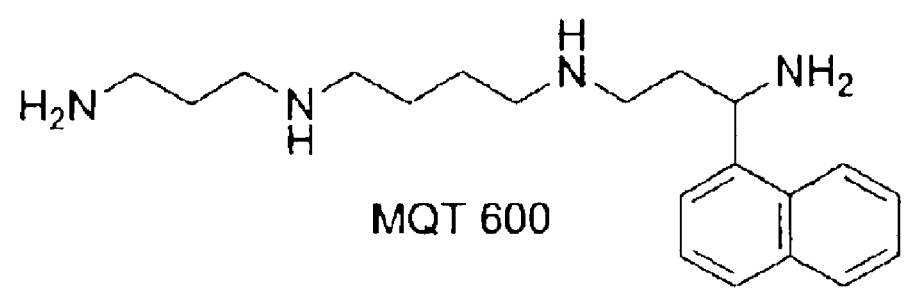
MQT 600

Fig. 3

| Analog | Diamine Relationship | Structure | Distance between cyclohexane diamines | Conformational Representation |
|---|---|---|---|---|
| 200-1 | 1,4-cis | (structure) | 4.68 Å | |
| 200-2 | 1,4-trans | (structure) | 5.73 Å | |
| 200-3 | 1,3-cis | (structure) | 4.89 Å | |
| 200-4 | 1,3-trans | (structure) | 4.36 Å | |
| 200-5 | 1,2-cis | (structure) | 2.83 Å | |
| 200-6 | 1,2-trans | (structure) | 2.84 Å | |

Fig. 5

| SERIES 300 ANALOGS | | | |
|---|---|---|---|
| NAME | b | c | Structure |
| 300-1 | 0 | 0 | cyclohexyl-NH-CH₂CH₂-NH-CH₂CH₂-NH₂ (with NH₂ on cyclohexyl) |
| 300-2 | 0 | 2 | cyclohexyl(NH₂)-NH-CH₂CH₂-NH-(CH₂)₄-NH₂ |
| 300-3 | 0 | 5 | cyclohexyl(NH₂)-NH-CH₂CH₂-NH-(CH₂)₇-NH₂ |
| 300-4 | 0 | 10 | cyclohexyl(NH₂)-NH-CH₂CH₂-NH-(CH₂)₁₂-NH₂ |
| 300-5 | 1 | 1 | cyclohexyl(NH₂)-NH-(CH₂)₃-NH-(CH₂)₃-NH₂ |
| 300-6 (MQT 100) | 1 | 4 | cyclohexyl(NH₂)-NH-(CH₂)₃-NH-(CH₂)₆-NH₂ |
| 300-7 | 1 | 6 | cyclohexyl(NH₂)-NH-(CH₂)₃-NH-(CH₂)₈-NH₂ |
| 300-8 | 2 | 4 | cyclohexyl(NH₂)-NH-(CH₂)₄-NH-(CH₂)₆-NH₂ |
| 300-9 | 3 | 2 | cyclohexyl(NH₂)-NH-(CH₂)₅-NH-(CH₂)₄-NH₂ |
| 300-10 | 3 | 6 | cyclohexyl(NH₂)-NH-(CH₂)₅-NH-(CH₂)₈-NH₂ |

Fig. 5 (Cont'd)
| NAME | b | c | Structure |
|---|---|---|---|
| 300-11 | 3 | 12 | 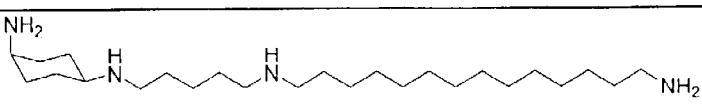 |
| 300-12 | 5 | 0 | 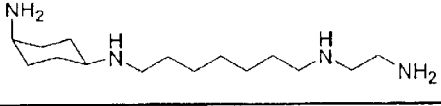 |
| 300-13 | 5 | 3 | 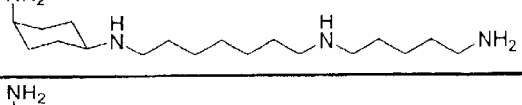 |
| 300-14 | 5 | 11 | 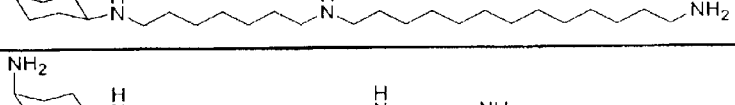 |
| 300-15 | 7 | 1 | 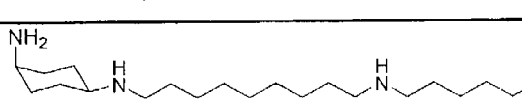 |
| 300-16 | 7 | 5 | 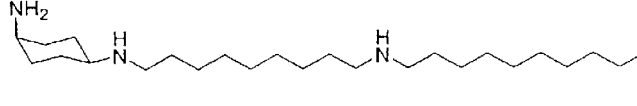 |
| 300-17 | 7 | 11 | 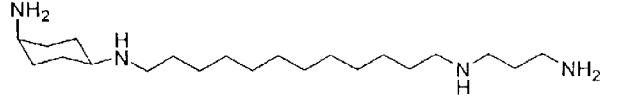 |
| 300-18 | 10 | 1 | 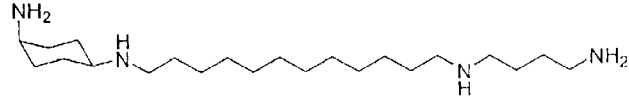 |
| 300-19 | 10 | 2 | 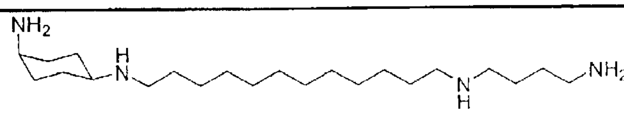 |
| 300-20 | 10 | 7 | 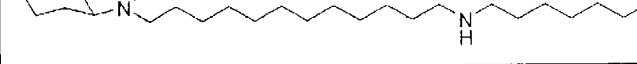 |

Fig. 5 (Cont'd)
| Series 400 Analogs | | |
|---|---|---|
| NAME | b | Structure |
| 400-1 | 0 | 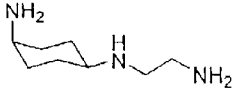 |
| 400-2 | 1 | 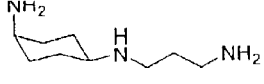 |
| 400-3 | 2 | 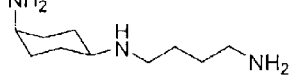 |
| 400-4 | 3 | 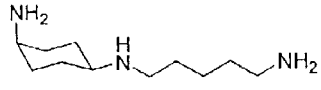 |
| 400-5 | 5 | 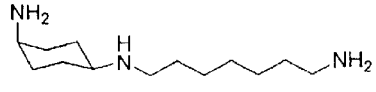 |
| 400-6 | 6 | 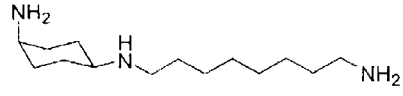 |
| 400-7 | 10 | 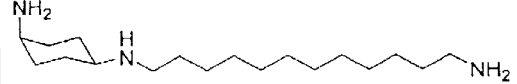 |
| 400-8 | 12 | 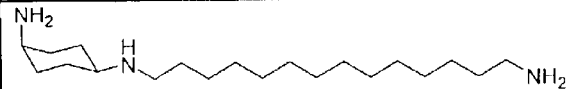 |

Fig. 6
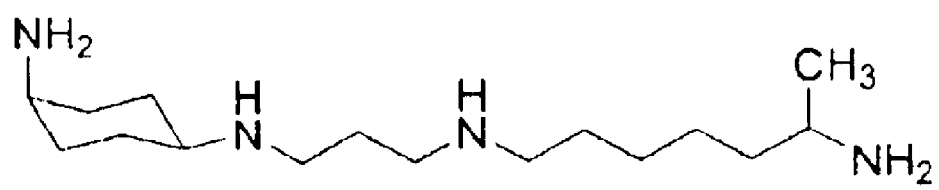
MQT 100 - methyl
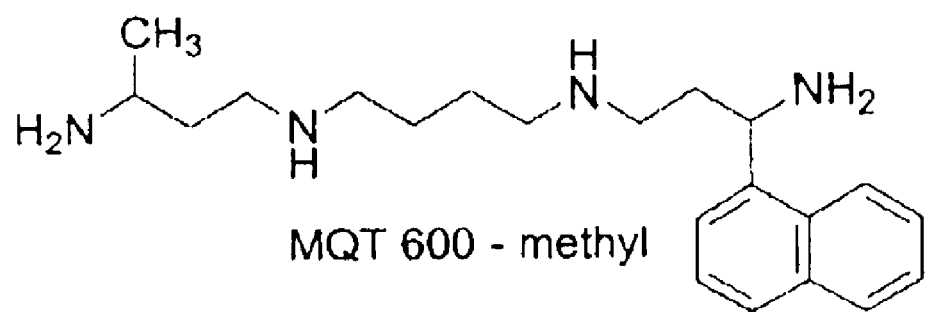
MQT 600 - methyl

| | | |
|---|---|---|
| 600-7 | Structure with naphthalene, OCH₃, HO, NPth groups | Polyamine chain with naphthalene-OCH₃ terminus |
| 600-8 | Tetrahydroisoquinoline with N-Bz, HO | Polyamine with tetrahydroisoquinoline terminus |
| 600-9 | Quinoline (4-position) with HO, NPth | Polyamine with quinoline terminus |
| 600-10 | Quinoline (2-position) with HO, NPth | Polyamine with quinoline terminus |
| 600-11 | 2-Naphthyl with HO, NPth | Polyamine with 2-naphthyl terminus |
| 600-12 | 1-Naphthyl with HO, NPth | Polyamine with 1-naphthyl terminus |
| 600-13 | Styryl-phenyl with HO, NPth | Polyamine with styryl-phenyl terminus |

Fig. 9 (Cont'd)

| | | |
|---|---|---|
| 600-14 | HO-CH(NPth)-C6H4-CH=CH-C6H5 (structure) | H2N-(CH2)3-NH-(CH2)4-NH-(CH2)2-CH(NH2)-C6H4-CH=CH-C6H5 (structure) |
| 600-15 | HO-CH2-CH(NPth)-C6H5 (structure) | H2N-(CH2)3-NH-(CH2)4-NH-CH2-CH(NH2)-C6H5 (structure) |
| 600-16 | HO-CH2-CH2-CH(NPth)-(2-furyl) (structure) | H2N-(CH2)3-NH-(CH2)4-NH-(CH2)2-CH(NH2)-(2-furyl) (structure) |
| 600-17 | HO-CH2-CH2-CH(NPth)-(2-thienyl) (structure) | H2N-(CH2)3-NH-(CH2)4-NH-(CH2)2-CH(NH2)-(2-thienyl) (structure) |
| 600-18 | HO-CH2-CH2-CH(NPth)-(1-naphthyl) (structure) | H2N-(CH2)4-NH-(CH2)3-NH-(CH2)2-CH(NH2)-(1-naphthyl) (structure) |
| 600-19 | HO-CH2-CH2-CH(NPth)-(1-naphthyl) (structure) | H2N-(CH2)3-NH-(CH2)3-NH-(CH2)2-CH(NH2)-(1-naphthyl) (structure) |
| 600-20 | HO-CH2-CH2-CH(NPth)-(1-naphthyl) (structure) | H2N-(CH2)5-NH-(CH2)3-NH-(CH2)2-CH(NH2)-(1-naphthyl) (structure) |

Fig. 10
| Analog | Precursor | Structure SERIES 700 analogs |
|---|---|---|
| 700-1 | 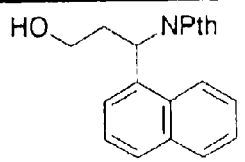 | 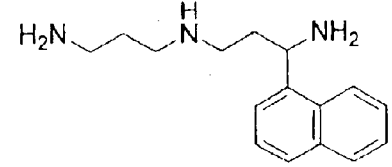 |
| 700-2 | 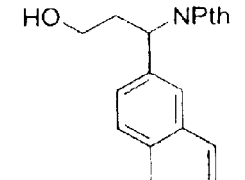 | 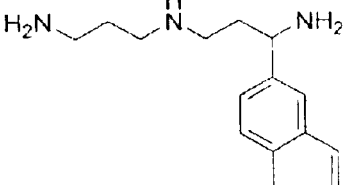 |
| 700-3 | 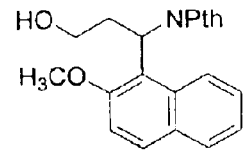 | 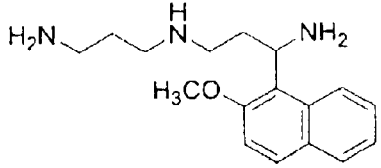 |
| 700-4 | 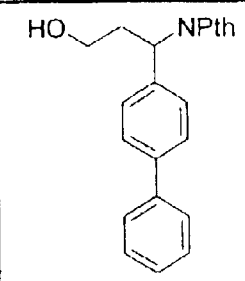 | 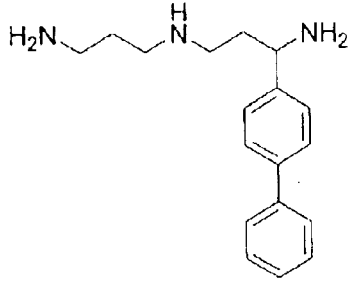 |
| 700-5 | 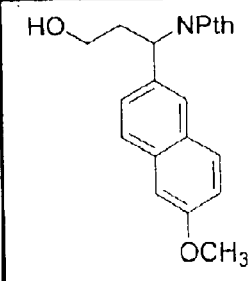 | 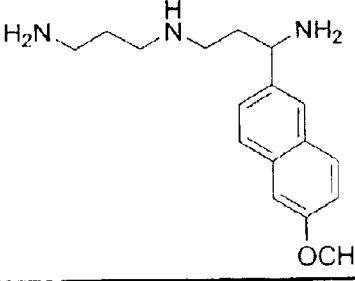 |
| 700-6 | 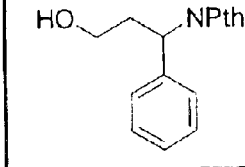 | 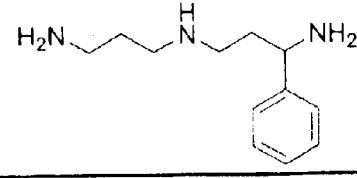 |

| | | |
|---|---|---|
| 700-14 | HO–CH(NPth)–CH2– attached to 4-(phenylvinyl)phenyl group (stilbene) | H2N–(CH2)3–NH–(CH2)2–CH(NH2)– attached to 4-(phenylvinyl)phenyl group |
| 700-15 | HO–CH2–CH(NPth)–phenyl | H2N–(CH2)3–NH–CH2–CH(NH2)–phenyl |
| 700-16 | HO–CH2–CH2–CH(NPth)– attached to 2-furyl | H2N–(CH2)3–NH–(CH2)2–CH(NH2)– attached to 2-furyl |
| 700-17 | HO–CH2–CH2–CH(NPth)– attached to 2-thienyl | H2N–(CH2)3–NH–(CH2)2–CH(NH2)– attached to 2-thienyl |
| 700-18 | HO–CH2–CH2–CH(NPth)– attached to 1-naphthyl | H2N–(CH2)4–NH–(CH2)2–CH(NH2)– attached to 1-naphthyl |
| 700-19 | HO–CH2–CH2–CH(NPth)– attached to 1-naphthyl | H2N–(CH2)3–NH–(CH2)2–CH(NH2)– attached to 1-naphthyl |
| 700-20 | HO–CH2–CH(NPth)– attached to 1-naphthyl | H2N–(CH2)5–NH–(CH2)2–CH(NH2)– attached to 1-naphthyl |

Fig. 11
SERIES 800 Examples
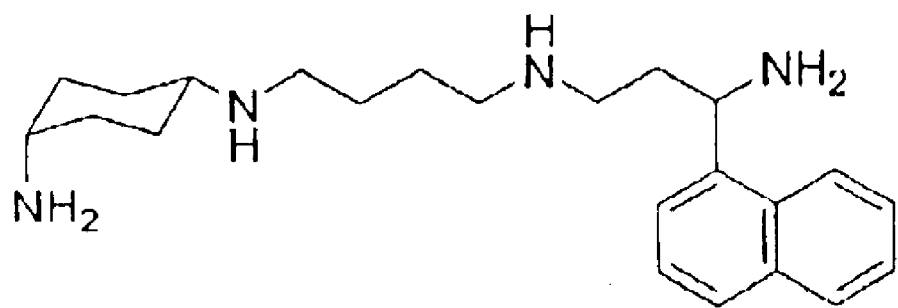
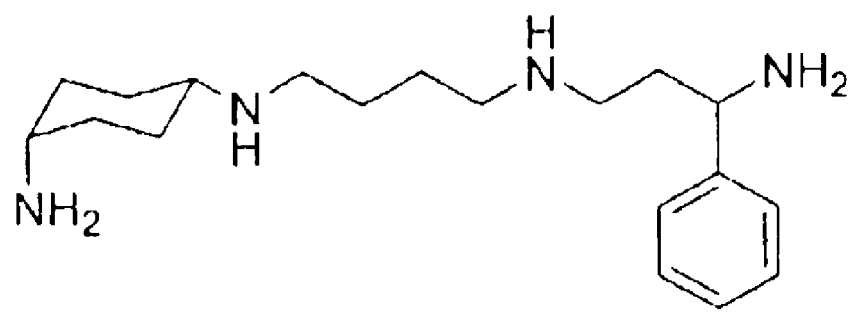

Fig. 14

| SERIES | DESCRIPTION | NUMBER OF ANALOGS |
|---|---|---|
| 100 | Cis/trans regioisomers of cyclic portion | 6 in cyclohexane series |
| 200 | Truncations of above analogs | 6 in cyclohexane series |
| 300 | Amino walk of Series 100 analogs | 1014 (- 6 above) = 1008 (analogs using b, c = 0 to 12) |
| 400 | Truncated amino walk of Series 100 analogs | 78 (- 6 above) = 72 (analogs using b = 0 to 12) |
| 500 | Methylated "metabolo-proof" | > 2 |
| 600 | Aromatic substituted | 20 shown 20x13x13x13=43940 (analogs with amino-walk using a, b or c = 0 to 12) |
| 700 | Truncated Aromatic substituted | 20 shown 20x13x13=3380 (analogs with amino-walk using b or c = 0 to 12) |
| 800 | Combination Analogs | > 1 |

FIG. 15

| Compound | Cell growth inhibition IC$_{50}$ (μM) | TNFα inhibition EC$_{50}$ (μM) |
|---|---|---|
| MQT 100 | >100 | 6.3 ± 1.7 |
| MQT 600 | >100 | 4.4 ± 3.8 |

IMMUNOMODULATION WITH NOVEL PHARMACEUTICAL COMPOSITIONS

FIELD OF THE INVENTION

The present invention relates to the synthesis and use of a novel class of tumor necrosis factor (TNFα) inhibitors and immunomodulators. These compounds have pharmacological applications as well as uses in assays relating to TNFα and other involved cytokines. As pharmaceuticals, these compounds are used to treat inflammatory, infectious, autoimmune or other proliferative diseases and conditions related to the unwanted presence or activity of TNFα and/or one or more other involved cytokines, alone or in combination with other agents.

BACKGROUND OF THE INVENTION

Exuberant production of pro-inflammatory cytokines has been implicated in the pathogenesis of numerous inflammatory and autoimmune diseases. Secretion of TNFα is a primary event in the initiation of the inflammatory cascade (Brennan F. M., et. al. *Lancet*, 1989, 2:244–7; Haworth C, et. al. *Eur. J. Immunol.* 1991, 21:2575–2579) and directly contributes to the initiation and maintenance of these diseases. Other pro-inflammatory cytokines also play a role, including interleukin 1β (IL-1β), IL-6, IL-8, IL-12 nitric oxide (NO), IFN-γ and granulocyte macrophage-colony stimulating factor (GM-CSF), while anti-inflammatory cytokines such as IL-10 may reduce disease. Cells of the immune system, macrophages in particular, secrete many of these cytokines in response to activating stimuli. Blocking pro-inflammatory cytokines and TNFα in particular has been shown to improve the symptoms and progression of a variety of inflammatory diseases. Thus, inhibition of either the production or the activity of TNFα and/or modulation of other cytokines active in the disease is an appealing therapeutic target for the treatment of inflammatory, infectious, autoimmune and other proliferative diseases and conditions.

Many inflammatory diseases have been treated with steroids, methotrexate, immunosuppressive drugs including cyclophosphamide, cyclosporine, azathioprine and leflunomide, nonsteroidal anti-inflammatory agents including aspirin, acetaminophen and cox-2 inhibitors, gold agents and anti-malarials. These drugs have a variety of disadvantages such as adverse reactions and lack of efficacy. New anti-TNFα biologic therapies have emerged that give a faster onset of relief and improved efficacy. However, these protein-based therapies also suffer drawbacks including adverse side effects such as injection site reactions, rash, upper respiratory infections, autoimmune disorders and serious infections. Another shortcoming of these biologic therapies is their required route of administration, intravenous (IV) or subcutaneous (SC), as opposed to more convenient and compliant oral or dermal routes. Accordingly, a need still exists for the development of novel small molecule compositions that inhibit TNFα and/or modulate the expression of one or more other cytokines that can be used to treat inflammatory, infectious, autoimmune and other proliferative diseases and conditions.

The pathogenesis of rheumatoid arthritis (RA), a chronic progressive inflammatory autoimmune disorder, is mediated by cytokines. Several cytokines, including TNFα (Di Giovine F. S., et. al. *Ann. Rheum. Dis.* 1988, 47:768–772) IL-1 (Rooney M., et. al. *Rheumatol Int.* 1990, 10:217–219), IL-10 (Arend W. P. et. al. *Arthritis. Rheum.* 1990, 30:305–315), and GM-CSF (Firestein G. S., et. al. *J Exp. Med.* 1988, 168:1573–1586.; Xu W. D., et. al. *J. Clin. Invest.* 1989, 83:876–882), are upregulated in the joints of RA patients with active disease. Elevated levels of TNFα and IL-1β can contribute to joint swelling seen in experimental animal models of arthritis and human RA (Thorbecke, G. J. et. al. *Proc. Natl. Acad. Sci.,* 1992, 89:7375–7379; Chu C. Q., et. al. *Arth. Rheum.* 1991, 34:1125–1132.; Farahat M. N., et. al. *Ann. Rheum. Dis.* 1993, 52:870–875; Brennan F. M., et. al. *Eur J. Immunol.* 1992, 22:1907–1912; Elliott M. J., et. al. *Baillieres Clin. Rheumatol.* 1995, 9:633–652). Anti-TNFα therapy using both antibodies and fusion proteins against TNFα has been shown to reduce the symptoms of collagen-induced arthritis in mice (Williams, R. O., et. al. *Proc. Natl. Acad. Sci.,* 1992, 89:9784–9788; Wooley P. H., et. al. *J Immunol,* 1993, 151:6602–6607; Mori L., et. al. *J Immunol,* 1996, 157:3178–3182) and in human clinical settings (Elliott M. J., et. al. *Arth Rheum.* 1993, 36:1681–1690; Elliott M. J., et. al. *Lancet,* 1994, 344:1105–1110; Elliott M. J., et. al. *Lancet,* 1994; 344:1125–1127; Moreland L. W., et. al. *N. Engl J. Med.* 1997, 337:141–147; Moreland L. W., et. al. *J. Rheumatol.* 1996, 23:1849–55; Rankin E. C., et. al. *Br. J. Rheumatol.* 1995, 34:334–42; Sander O., et. al. *Arth. Rheum.* 1996, 39 (suppl.):S242 (Abstract)). Recently, anti-IL-1β therapy using a recombinant IL-1 receptor antagonist has been shown efficacious in combination with methotrexate in treating RA patients (Cohen S., et. al. *Arth. Rheum.* 2002, 46:614–624). In experimental animal models of arthritis, inhibition of NO production (Brahn E., et. al. *J. Rheumatol.* 1998, 25:1785–1793), blockage of GM-CSF activity (Cook A. D., et. al. *Arth. Res.* 2001, 3:293–298) or treatment with recombinant IL-10 (an anti-inflammatory cytokine) (Tanaka T., et. al. *Inflamm. Res.* 1996; 45:283–288) reduced arthritic symptoms. These studies underscore the contribution of individual cytokines to the pathogenesis of RA and imply that therapies that target more than one cytokine or a selective subset of cytokines may be more efficacious.

Therapies that target TNFα have been shown to be effective in other inflammatory diseases in humans and in animal models of human disease. Anti-TNFα therapy has been used to effectively treat Crohn's disease, a chronic inflammatory bowel disease. Infliximab (Remicade, Centocor, Inc.), an intravenously administered monoclonal antibody to TNFα, has been approved for commercial use in refractory Crohn's disease. Mixed results have been seen in patients receiving Etanercept (Enbrel, Amgen Corp.), an injectable TNFα receptor fusion protein. In a small study, patients responded favorably and had decreased inflammatory markers (D'Haens G. et. al. *Am J Gastroenterol.* 2001, 96:2564–2568) following treatment with this drug. In a different study, Etanercept was found to be ineffective for the treatment of patients with moderate to severe Crohn's disease (Sandborn W. J., et. al. *Gastroenterology* 2001, 121:1088–1094). The reasons for lack of efficacy could be mechanistic, dose-related or may indicate that the biologic drug did not reach the target cell population. Another TNFα modulator, the small molecule thalidomide, which both down-regulates TNFα production and inhibits angiogenesis, has been shown to relieve experimental iodoacetamide-induced colitis in rats (Kenet G., et. al. *Isr. Med. Assoc. J.* 2001, 9:644–648). Additionally, early findings in a long-term treatment protocol involving children and young adults treated with thalidomide suggest that treatment resulted in decreased Crohn's disease activity (Facchini S., et. al. *J Pediatr. Gastroenterol. Nutr.* 2000, 32:178–181).

Spondyloarthropathies (SpA) are a group of related disorders with varying clinical symptoms including spondylitis, synovitis, psoriatic arthritis and subclinical gut inflammation. TNFα appears to play a strong role in the pathogenesis of these syndromes and heightened concentrations of TNFα are found in the joint, skin and gut of patients afflicted with SpA. Etanercept has been approved for treatment of psoriatic arthritis. Infliximab used in two open studies demonstrated significant clinical benefit against SpA (Van den Bosch F., et. al. *Ann. Rheum. Dis.* 2000, 59:428–433; Baete D., et. al. *Arhritis. Rheum.* 2001, 44:186–95) and psoriatic arthritis (Ogilvie A. L. et al, Br. J. Dermatol. 2001, 144:587–589). The common mechanism of action of these drugs and their mutual ability to improve clinical outcome suggest that anti-TNFα therapy is useful in the treatment of SpA.

The local release of TNFα contributes to the inflammatory skin disease psoriasis. Concentrations of TNFα and soluble TNFα receptors (p55 and p75) were higher in lesional stratum corneum extracts of psoriatic patients than controls (Ettehadi P., et. al. *Clin. Exp. Immunol.* 1994, 96:146–151). These results confirm the presence of immunoreactive TNFα and quantifiable concentrations of soluble TNF receptors, which may regulate the effects of TNFα. A number of case reports and small clinical studies indicate that infliximab improved psoriasis symptoms (Chaudhari U., et. al. *Lancet* 2001, 357:1842–1847; Newland M. R., *Int. J. Dermatol.* 2002, 41:449–452; Schopf R. E., et. al. *J. Am. Acad. Dermatol.* 2002, 46:886–91). Etanercept has also been clinically evaluated and shows efficacy against psoriasis symptoms. Biologically active IL-1β has also been found in psoriatic scales (Lundqvist E. N., et. al. *Eur. J. Immunol.* 1997, 27:2165–2171) suggesting a role for this cytokine in the pathogenesis of psoriasis. Again, the interaction of various cytokines appears to be important in this disease and suggests that efficacious treatments would target a variety of cytokines.

Overproduction of TNFα also contributes to the clinical features of numerous autoimmune diseases such as diabetes. Therapies directed at TNFα have been shown to provide clinical benefit in Type II diabetes. For example, thiazolidinedione derivatives are a class of drugs that activate the peroxisome proliferator-activated receptor-gamma (PPARγ) resulting in diminished macrophage activation and decreased production of TNFα (Ricote M., et. al. *Nature* 1998, 391:79–82; Jiang C., et. al. *Nature* 1998, 391:82–86). These drugs have been tested in various human clinical studies in non-insulin-dependent diabetes and these drugs improved control of glucose metabolism and blood lipid profiles (Kumar S., et. al. *Diabetologia* 1996, 39:701–709; Berkowitz K., et. al. *Diabetes* 1996, 45:1572–1579; Yamasaki Y. et. al. *Tohoku J. Exp. Med.* 1997, 183:173–183) in addition to lowering TNFα levels in plasma (Katsuki A., et. al. *Diabete. Obes. Metab.* 2000, 2:189–2191).

Systemic lupus erythematosus (SLE) is another autoimmune disorder precipitated by increased TNFα levels. Within lupus patients, serum C-reactive protein, IL-1β and TNFα levels were higher than in controls suggesting that an over-exuberant immune response plays a role in the disease (Liou L. B. *Clin. Exp. Rheumatol.* 2001, 19:515–523). A study of patients with one form of SLE, neuropsychiatric lupus erythematosus (NPLE), showed that the number of peripheral blood mononuclear cells expressing mRNA for TNFα as well as the cerebrospinal fluid level of NO metabolites correlated with NPLE disease severity (Svenungsson E., et al. *Ann. Rheum. Dis.* 2001, 60:372–9). In a study by Segal, (Segal R., et. al. *Lupus* 2001, 10:23–31), SLE was induced in mice with human anti-DNA antibodies. These mice were then treated with an anti-TNFα antibody or pentoxifylline, a phosphodiesterase inhibitor that lowers TNFα production. Both treatments reduced the production of TNFα and lowered serum levels of anti-DNA antibodies. The anti-inflammatory cytokine IL-10 has been shown to regulate murine models of lupus. IL-10$^{-/-}$ knockout mice were bred into a lupus susceptible mouse strain. These mice developed more severe lupus and suffered higher mortality than IL-10$^{+/+}$ mice (Yin Z., et. al. *J. Immunol.* 2002, 169:2148–2155). An ideal SLE therapy would target multiple cytokines; inhibiting TNFα levels while enhancing or exerting no inhibition on IL-10 levels.

TNFα is also involved in cutaneous forms of lupus. A-308A polymorphism of the human TNFα promoter has a significantly increased prevalence in patients suffering from subacute cutaneous LE. This polymorphism led to substantially higher induction of TNFα after exposure to UVB than wild type, contributing to the photosensitivity seen in this disease (Werth V. P., et. al. *J. Invest. Dermatol.* 2000, 115:726–730). Biopsies from patients with localized discoid LE showed significantly elevated levels of IL-2 and IFNγ mRNA and elevated levels of TNFα mRNA compared to normal skin (Toro J. R., et. al. *Arch. Dermatol.* 2000, 136:1497–1501). Overall, these findings suggest that anti-TNFα therapy would benefit patients with these forms of LE.

Multiple sclerosis is an inflammatory demyelinating disease of the central nervous system characterized by a T-cell mediated autoimmune response to the myelin sheath. A number of pro-inflammatory cytokines contribute to the ongoing inflammation in human disease (Sharief M. K., et. al. *N. Engl. J. Med.* 1991, 325:467–472) and murine experimental autoimmune encephalomyelitis (EAE) models (Conlon P., et. al. *Neurobiol. Dis.* 1999, 6:149–66). Administration of anti-TNFα antibodies in the EAE animal model reversed demyelination and paralysis (Selmaj K., et. al. *Ann. Neurol.* 1991, 30:694–700; Karin N., et. al. *J. Exp. Med.* 1994, 180:2227–37). Human trials with monoclonal antibodies and soluble TNFα receptor have been unsuccessful, emphasizing the need to develop new anti-TNFα therapies (van Oosten, B. W. et. al. *Neurology* 1996, 47:1531–1534).

TNFα has also been found to potently upregulate human immunodeficiency virus 1 (HIV-1) expression in T cell clones (Duh E. J., et. al. *Proc. Natl. Acad. Sci. USA* 1989, 86:5974–8; Folks T. M., et. al. *Proc. Natl. Acad. Sci. USA* 1989, 86:2365–2368; Clouse K. A., et. al. *J Immunol.* 1989, 142:431–8.) and monocytes (Koyanagi Y., et. al. *Science* 1988, 241:1673–1675). TNFα enhances HIV-1 replication in T cells by increasing the surface density of the HIV docking receptor, CXCR4 (Biswas P., et. al. *Cytokine* 2001, 13:55–59). In vivo effects of TNFα were demonstrated in a study using homozygous HIV-1 transgenic mice. These mice have significantly increased serum TNFα levels and die within 3–4 weeks. Treatment with an antibody to TNFα prevented death, decreased characteristic skin lesions in these mice, and profoundly reduced HIV-1 expression (De S. K., et. al. *J. Virol.* 2002, 76:11710–4). Thus, inhibition of TNFα could suppress T cell activation, CXCR4 expression and slow viral spread and replication.

Pro-inflammatory cytokines have been implicated in other viral infections including the cytomegalovirus, influenza virus and the herpes family of viruses. TNFα enhances the basal activity of the major immediate early enhancer/promoter of human cytomegalovirus and may play a role in reactivation of latent HCMV infection in premonocytic cells (Prosch S., et. al. *Virology* 1995, 208:197–206). Likewise, GM-CSF enhanced de novo influenza A virus protein synthesis, viral particle release and cell death in human monocytes infected by influenza A virus. Treatment of persistently herpes simplex virus (HSV) infected macrophages for 2 weeks with TNFα resulted in an increase of HSV yield and an increase in virus-induced cytotoxic effects (Domke-Opitz I., et. al. *Scand. J. Immunol.* 1990, 32:69–75). Further studies showed that TNFα and possibly GM-CSF enhanced the reactivation frequency and replication of HSV in the trigeminal ganglia of mice latently infected with HSV (Walev I., et. al. *Arch. Virol.* 1995, 140:987–992).

A number of cytokines contribute to the demise of patients suffering from sepsis or endotoxic shock. TNFα and IL-1β have a well-established central role in sepsis, septic shock and endotoxic shock. Increased levels of these cytokines are associated with fever, hypotension and shock (Smith J. W. et. al. *J. Clin. Oncol.* 1992, 10:1141–1152; Chapman P. B., et. al. *J. Clin. Oncol.* 1987, 5:1942–1951) together with the induction of gene expression for phospholipase A2 (Gronich J., et. al. *J. Clin. Invest.* 1994, 93:1224–1233) and NO synthase. The induction of NO from smooth muscle cells mediates decreased mean arterial pressure and systemic vascular resistance during septic shock, suggesting a fundamental role for NO. Therapies targeting TNFα in particular with downregulatory effects on IL-1β and NO could be beneficial in the treatment of sepsis, septic shock, and endotoxic shock.

A variety of cell types are involved in the inflammatory process. Overproduction of TNFα by monocytes, macrophages and other immune cells is a key element in the pathogenesis of a multitude of diseases. Macrophages and T-cells in particular play a central role in the initiation and maintenance of the immune response. Once activated by pathological or immunogenic stimuli, macrophages respond by releasing a host of cytokines, including TNFα, IL-1β, IL-8, IL-12, NO, IL-6, GM-CSF, G-CSF, M-CSF and others. T-cells release IL-2, IL-4, interferon-γ, and other inflammatory cytokines. These cytokines activate other immune cells and some can also act as cytotoxic agents alone. Excessive release of macrophage and T-cell derived inflammatory mediators can therefore lead to damage of normal cells and surrounding tissues. The overabundance of these cytokines is a clinical feature of many chronic inflammatory diseases. Treatment and resolution of these conditions may depend on attenuation of the immune cells, particularly the macrophages and T-cells.

Previous reports suggest that polyamines modulate macrophage function by inhibiting the secretion of inflammatory mediators such as TNFα (Zhang M., et. al. *J. Exp. Med.* 1997, 185, 1759–68). Treatment of human peripheral blood mononuclear cells or a murine macrophage cell line with spermine prior to stimulation with the immunostimulant lipopolysaccharide (LPS) inhibited the release of pro-inflammatory cytokines including TNFα. Spermine treatment had no effect on increases in TNFα mRNA levels, indicating that the suppression occurred post-transcriptionally. In subsequent studies, Zhang et al reported that pretreatment of cells with a polyamine transport inhibitor prior to addition of spermine and LPS restored TNFα levels to those seen in the absence of spermine (Zhang M., et. al. *Mol. Med.* 1999, 5:595–605). The inhibitory action of spermine may provide a natural mechanism for attenuation of the immune response and protection against excessive inflammatory damage. Furthermore, a U.S. patent (Bergeron, R. J. U.S. Pat. No. 5,843,959) describes bicyclic polyamine compositions that exerted anti-inflammatory effects. These compositions provided modest inhibition of type II collagen-induced arthritis in mice and carrageenan-induced edema in rat paws. An additional U.S. patent (Tracey, K. J. et. al. U.S. Pat. No. 6,482,833) describes spermine antagonists that prevent spermine-induced immunosuppression. Thus the utility of polyamine analog-based therapies in treating inflammatory conditions has been established.

SUMMARY OF THE INVENTION

The present invention is directed to novel polyamine analogs and derivatives and methods for their use in the inhibition of the expression or activity of TNFα and/or one or more other cytokines including but not limited to IL-1β, IL-2, IL-6, NO, GM-CSF, interferon-γ(IFN-γ), G-CSF, M-CSF, IL-8, IL-12, and IL-18. The analog and derivative compounds of the invention have the ability to reduce detectable levels of TNFα produced or secreted by cells under conditions where TNFα production or secretion would occur. The compounds also may or may not have effects on other pro- or anti-inflammatory cytokines. Without being bound by theory, it is believed that the compounds of the invention inhibit the production or secretion of TNFα from cells under conditions where TNFα production or secretion would occur. The compounds of the invention may also inhibit the production or secretion of one or more other cytokines from cells under conditions where cytokine production or secretion would occur. They may be used independently or in combination with any other agent that exerts an effect against inflammatory, infectious, autoimmune or other proliferative diseases and conditions.

BRIEF DESCRIPTION OF THE DRAWINGS

FIG. 1 shows the structures of preferred compounds, MQT 100 and MQT 600.

FIG. 3 is a tabular representation of the conformational analysis of Series 200 analogs.

FIG. 5 is a tabular representation of representative series 300 and 400 "amino-walk" analogs.

FIG. 6 shows representative examples of methylated "metabolism-proof" molecules.

carbonyl)benzoate, $CH_3CN$, $H_2O$, $Na_2CO_3$; b) i. Isobutylchloroformate, $Et_3N$, THF ii. $NaBH_4$, MeOH.

Figure 9:
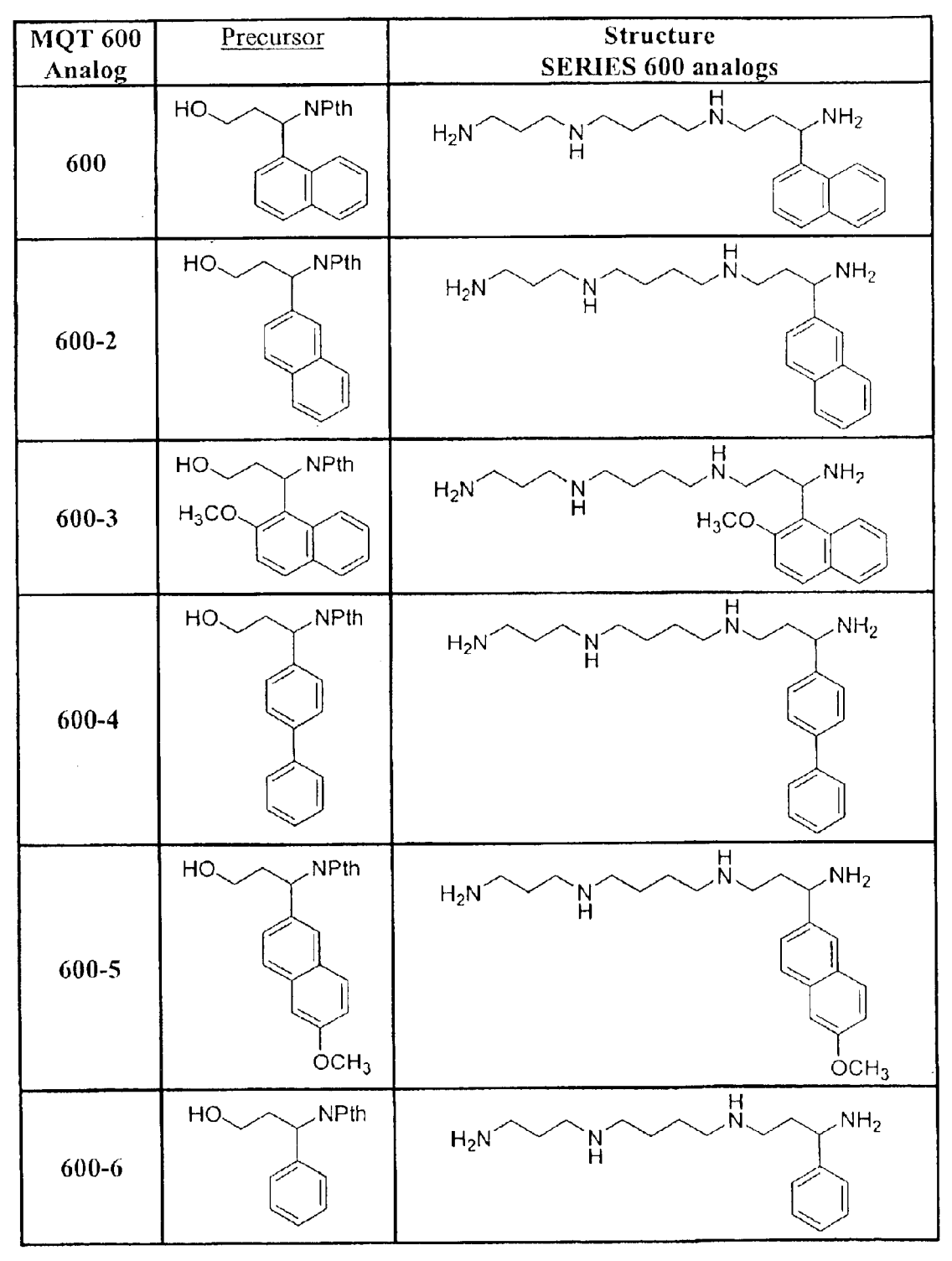

FIG. 9 is a tabular representation of precursors and examples of series 600 molecules.

Figure 10:
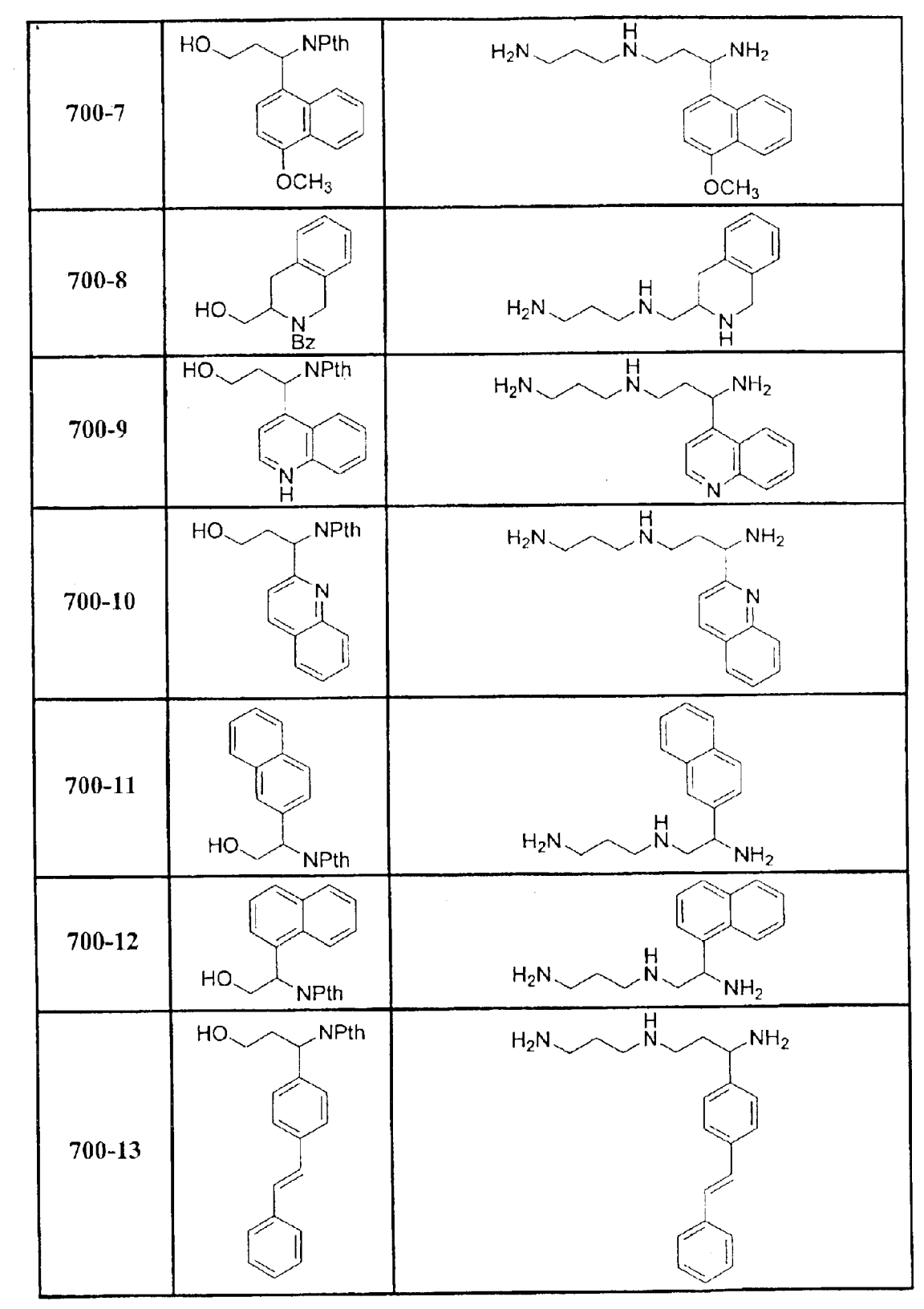

FIG. 10 is a tabular representation of series 700 analogs.

FIG. 11 shows the structure of two representative combination analogs (Series 800).

Figure 12:
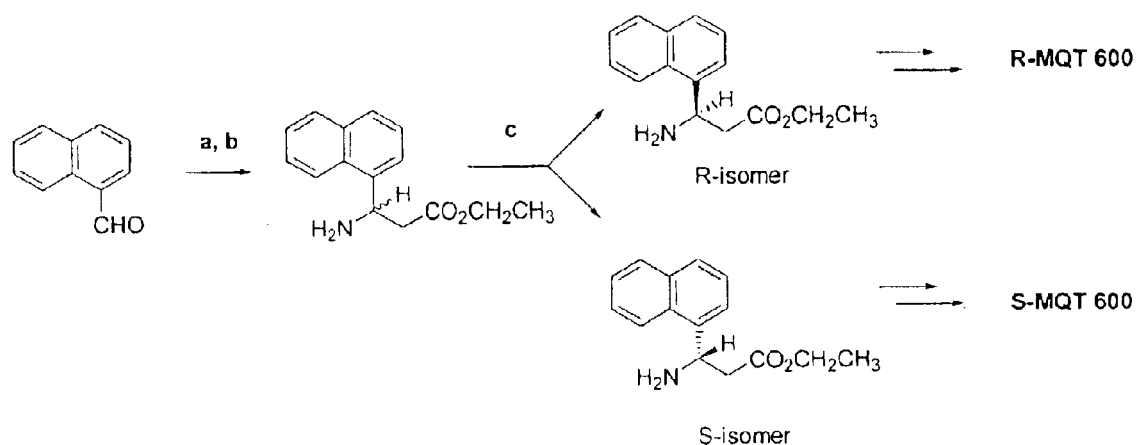

FIG. 12 shows the reaction scheme for the enzymatic resolution of MQT 600 stereoisomeric precursor mixture. Reagents and conditions: a) $NH_4OAc$, $CH_2(CO_2H)_2$, EtOH, reflux; b) $H_2SO_4$, EtOH, reflux; c) AmanoPS, $H_2O$.

Figure 13:
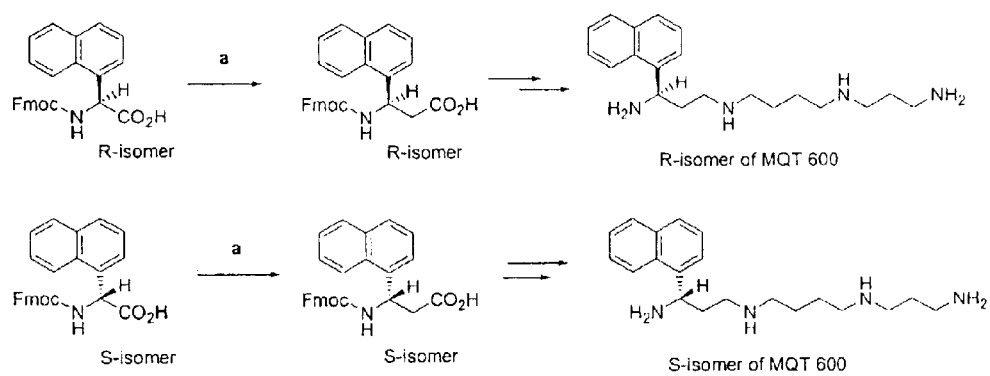

FIG. 13 shows the reaction scheme for the synthesis of MQT 600 enantiopure precursors via chemical synthesis from stereopure precursors. Reagents and conditions: a) i. $^iBuOCOCl$, N-methylmotpholine, THF, ii. $CH_2N_2$, ether; iii. $CF_3CO_2Ag$, N-methylmorpholine, $H_2O$, THF.

FIG. 14 is a tabular representation of the Analog Summary.

FIG. 15 shows the results from analysis of MQT 100 and MQT 600 for cell growth inhibition (referred to as $IC_{50}$) and inhibition of LPS-induced TNFα release into the extracellular environment (referred to as $EC_{50}$).

BEST AND VARIOUS MODES FOR CARRYING OUT INVENTION

The compounds and derivatives of the invention include those encompassed by the following formula I:

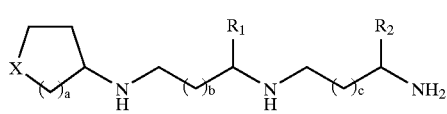

I.

wherein, a, b and c may be the same or different and are integers from 0 to 12, X equals NH or $CHNH_2$, $R_1$ and $R_2$ can be the same or different and equal to a hydrogen or a straight or branched $C_1$ to $C_{20}$ saturated or unsaturated aliphatic such as methyl; aliphatic amine; an alicyclic; single or multi-ring aromatic such as 1- or 2-naphthylene; a single or multi-ring aromatic heterocycle; a single or multi-ring saturated heterocycle and the halogenated forms thereof.

The compounds and derivatives of the invention also include those encompassed by the following formula II:

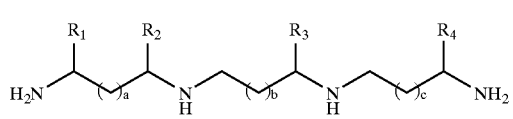

II.

wherein, a, b and c may be the same or different and are integers from 0 to 12; $R_1$, $R_2$, $R_3$, and $R_4$ can be the same or different and equal to a hydrogen or a straight or branched $C_1$ to $C_{20}$ saturated or unsaturated aliphatic such as methyl; aliphatic amine; an alicyclic; single or multi-ring aromatic such as 1- or 2-naphthylene; a single or multi-ring aromatic heterocycle; a single or multi-ring saturated heterocycle and the halogenated forms thereof.

A preferred aspect of the invention relates to a compound or derivative that is a potent inhibitor of inflammatory, infectious, autoimmune or other proliferative diseases and conditions by reducing or inhibiting the expression or secretion of TNFα outside the cell and/or modulating the expression or secretion of one or more other involved cytokines.

The present invention also provides for the free base or acid forms, as well as salts thereof, of the polyamine analogs and derivatives described herein. The invention also includes the optical isomers of the disclosed analogs and derivatives. In a further aspect of the invention, mixtures of enantiomers and/or diastereoisomers, resulting from a single preparative step, combination, or interconversion are encompassed.

The invention also provides for the prodrug forms of the above described analogs and derivatives, wherein the prodrug is metabolized in vivo to produce an analog or derivative as set forth above. Indeed, some of the above described analogs or derivatives may be a prodrug for another analog or derivative.

Listed below are definitions of various terms used to describe this invention. These definitions apply to the terms as they are used throughout this specification, unless otherwise limited in specific instances, either individually or as part of a larger group.

The term "aryl" refers to monocyclic or multiring aromatic hydrocarbon groups typically containing 6 to 14 carbon atoms in the ring portion, such as phenyl, naphthyl, biphenyl and diphenyl groups, each of which may be substituted.

The term "saturated aliphatic" refers to straight or branched chain unsubstituted hydrocarbon groups typically having 1 to 20 carbon atoms, more typically 1 to 8 carbon atoms. The expression "lower alkyl" refers to unsubstituted alkyl groups of 1 to 4 carbon atoms.

Examples of suitable saturated aliphatic or alkyl groups include methyl, ethyl and propyl. Examples of branched alkyl groups include isopropyl and t-butyl.

The term "halogen" or "halo" refers to fluorine, chlorine, bromine and iodine.

Examples of multiring aromatic (unsaturated) heterocycle groups are 2-quinolinyl, 3-quinolinyl, 5-quinolinyl, 6-quinolinyl, 7-quinolinyl, 1-isoquinolinyl, 3-isoquinolinyl, 6-isoquinolinyl, 7-isoquinolinyl, 3-cinnolinyl, 6-cinnolyl, 7-cinnolyl, 2-quinazolinyl, 4-quinazolinyl, 6-quinazolinyl, 7-quinazolinyl, 2-quinoxalinyl, 5-quinoxalinyl, 6-quinoxalinyl, 1-phthalaonyl, 6-phthalazinyl, 1–5-naphthyridin-2-yl, 1,5-naphthyridin-3-yl, 1,6-naphthyridin-3-yl, 1,6-naphthyridin-7-yl, 1,7-naphthyridin-3-yl, 1,7-naphth7yridin-6-yl, 1,8-naphthyrdiin-3-yl, 2,6-naphthyridin-6-yl, 2,7-naphthyridin-3-yl, indolyl, 1H-indazolyl, purinyl and pteridinyl.

Examples of single ring heterocycle groups are pyrrolyl, pyranyl, oxazolyl, thiazoyl, thiophenyl, furanyl, imidazolyl, pyrazolyl, pyridinyl, pyrazinyl, pyrimidinyl, pyridazinyl, isothiazolyl and isoxazolyl.

Examples of saturated heterocycle groups are pyrrolidinyl, imidazolidinyl, pyrazolidinyl, piperidinyl, piperazinyl, and morpholinyl.

The heterocycle groups contain N, O and/or S and typically contain 5 to 10 atoms in the ring(s).

Examples of suitable alicyclic groups are cyclopropyl, cyclobutyl, cyclopentyl and cyclohexyl.

Examples of suitable aliphatic amine groups are methylamine, ethylamine, propylamine, isopropylamine, tert-butyl amine and diethylamine. The amine groups include diamines, and triamines and can be primary, secondary or tertiary amines.

Typically the amines 1–20 contain carbon atoms and more typically 1–8 carbon atoms.

The compounds of the present invention can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

Prodrug forms of the compounds bearing various nitrogen functions (amino, hydroxyamino, hydrazino, guanidino, amidino, amide, etc.) may include the following types of derivatives where each R group individually may be hydrogen, substituted or unsubstituted alkyl, aryl, alkenyl, alkynyl, heterocycle, alkylaryl, aralkyl, aralkenyl, aralkynyl, cycloalkyl or cycloalkenyl groups as defined above.

Carboxamides, —NHC(O)R

Carbamates, —NHC(O)OR (Acyloxy)alkyl Carbamates, NHC(O)OROC(O)R

Enamines, —NHCR(=CHCRO$_2$R) or —NHCR(=CHCRONR$_2$)

Schiff Bases, —N=CR$_2$

Mannich Bases (from carboximide compounds), RCONHCH$_2$NR$_2$

Preparations of such prodrug derivatives are discussed in various literature sources (examples are: Alexander et al., J. Med. Chem. 1988, 31, 318; Aligas-Martin et al., PCT WO pp/41531, p. 30). The nitrogen function converted in preparing these derivatives is one (or more) of the nitrogen atoms of a compound of the invention.

Prodrug forms of carboxyl-bearing compounds of the invention include esters (—CO$_2$R) where the R group corresponds to any alcohol whose release in the body through enzymatic or hydrolytic processes would be at pharmaceutically acceptable levels.

Another prodrug derived from a carboxylic acid form of the invention may be a quaternary salt type

III.

of structure described by Bodor et al., J. Med. Chem. 1980, 23, 469.

It is of course understood that the compounds of the present invention relate to all optical isomers and stereoisomers at the various possible atoms of the molecule.

The compounds of this invention form acid and base addition salts with a wide variety of organic and inorganic acids and bases and includes the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkonic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, cabrate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include sodium hydroxide, potassium hydroxide, ammonium hydroxide, potassium carbonate, methylamine, diethylamine, and ethylene diamine.

The compounds may be utilized alone or in combination with other agents, particularly other inhibitors of polyamine synthesis or transport, but including other inhibitors of cell proliferation.

In another aspect of the invention, compositions containing the above described compounds and derivatives are provided. Preferably, the compositions are formulated to be suitable for pharmaceutical or agricultural use by the inclusion of appropriate carriers or excipients and/or anti-inflammatory agents.

In another aspect of the invention, compositions containing the disclosed analogs and derivatives are provided. Preferably, the compositions are formulated to be suitable for pharmaceutical use by the inclusion of one or more appropriate carriers or excipients.

In a further aspect of the invention, methods for the use of the above described analogs and derivatives, as well as compositions, are provided. These methods include uses of the invention's compounds to inhibit, retard or modulate the production, secretion, expression and/or activity of TNFα and/or one or more other involved cytokines to treat conditions associated with the unwanted or undesirable presence or activity of TNFα and/or one or more other involved cytokines. Examples of human diseases and conditions include, but are not limited to, chronic or acute inflammation, inflammatory bowel disease (including Crohn's disease), inflammatory bowel syndrome, autoimmune diseases, rheumatoid arthritis, systemic lupus erythematosus, cutaneous forms of lupus, diabetes, multiple sclerosis, psoriasis, spondyloarthropathies (SpA) including spondylitis, synovitis, psoriatic arthritis and subclinical gut inflammation and infectious diseases including sepsis, septic shock, endotoxic shock, HIV and other viral infections including cytomegalovirus, herpes simplex virus, influenza virus and other proliferative diseases and disorders including but not limited to cancer.

A preferred compound according to the present invention is designated as MQT 100 which is shown in FIG. 1. This compound inhibited TNFα production in a reproducible and robust manner. Another preferred compound is shown in FIG. 1 and designated as MQT 600.

Figure 2:
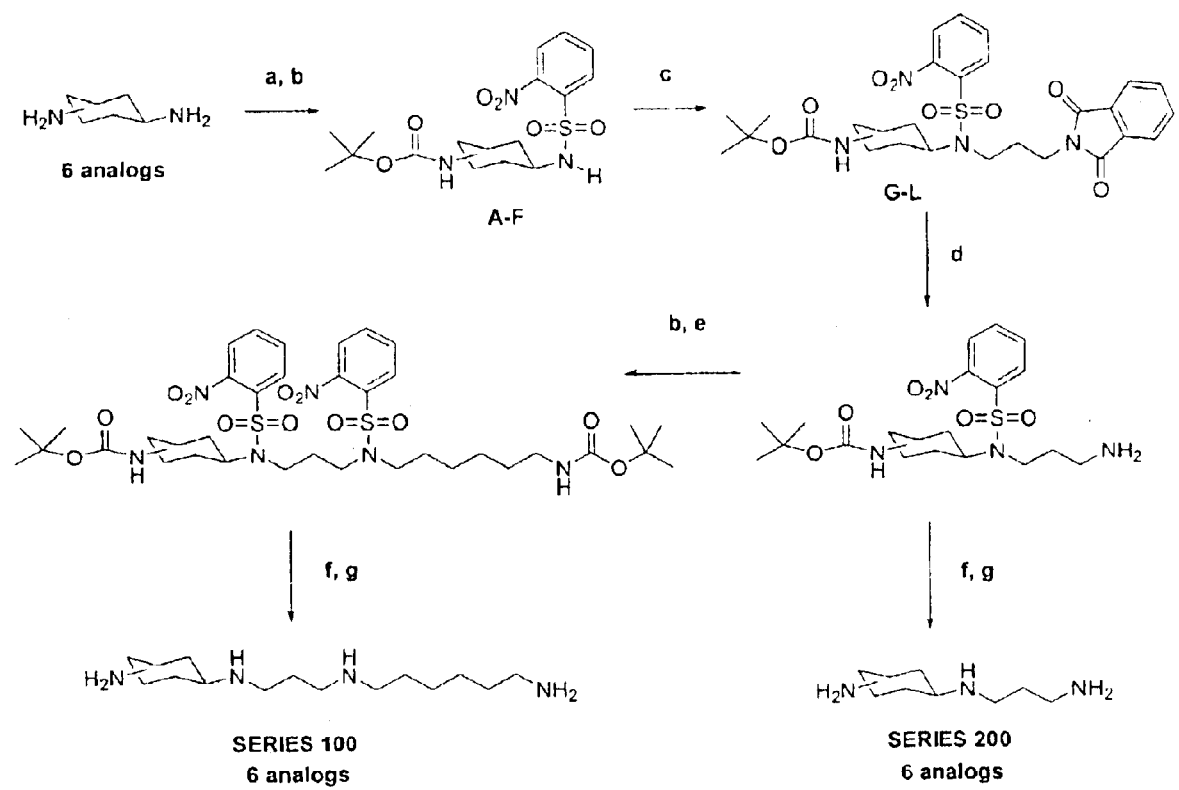
FIG. 2 shows the reaction scheme for the synthesis of analogs of MQT 100 (Series 100 and 200). Reagents and conditions: a) $Boc_2O$, $Na_2CO_3$, $THF/H_2O$; b) 2-nitrobenzenesulfonyl chloride, $CH_2Cl_2$, $Et_3N$; c) N-phthalimido-3-amino-1-propanol, $Ph_3P$, DIAD, THF; d) $NH_2NH_2$, EtOH, reflux; e) N-Boc-6-amino-1-hexanol, $Ph_3P$, DIAD, THF; f) $HSCH_2CH_2OH$, DBU, DMF; g) 3N HCl in MeOH.

The potent molecule MQT 100 as well as analogs thereof (e.g., series 100 and 200) can be synthesized via the route shown in FIG. 2. The synthetic route began by taking the six possible different isomers of diaminocyclohexane and mono-protecting them as their mono-$^t$butoxycarbonyl carbamates followed by derivatization with a 2-nitrobenzenesulfonyl group (Fukuyama, T., et. al. *Tetrahedron Lett.* 1997, 38, 5831–5834) to give intermediates A-F. These intermediates were then each individually coupled to N-(3-hydroxypropyl)phthalimide via a Mitsunobu reaction to give orthogonally protected intermediates G-L. Compounds G-L were used to produce two different series of final products. In one case, they were simply deprotected to give the six truncated analogs in SERIES 200. In the other series, G-L were subjected to another round of Mitsunobu extension with N-Boc-6-amino-1-hexanol to give analogs in SERIES 100 following their deprotection.

This series was tested for bioactivity and the results can be related to the arrangement of the two amino groups attached to the cyclohexane ring. Conformational analysis of this ring arrangement shows that the energy-minimized (performed using CambridgeSoft Chem3D version 5.0) structures have dramatically different spacing of these two groups. FIG. 3 shows the resulting structures for Series 200 together with the designations given them for convenience. The distance between these two amino groups as measured in the minimized structure are shown in FIG. 3.

Figure 4:
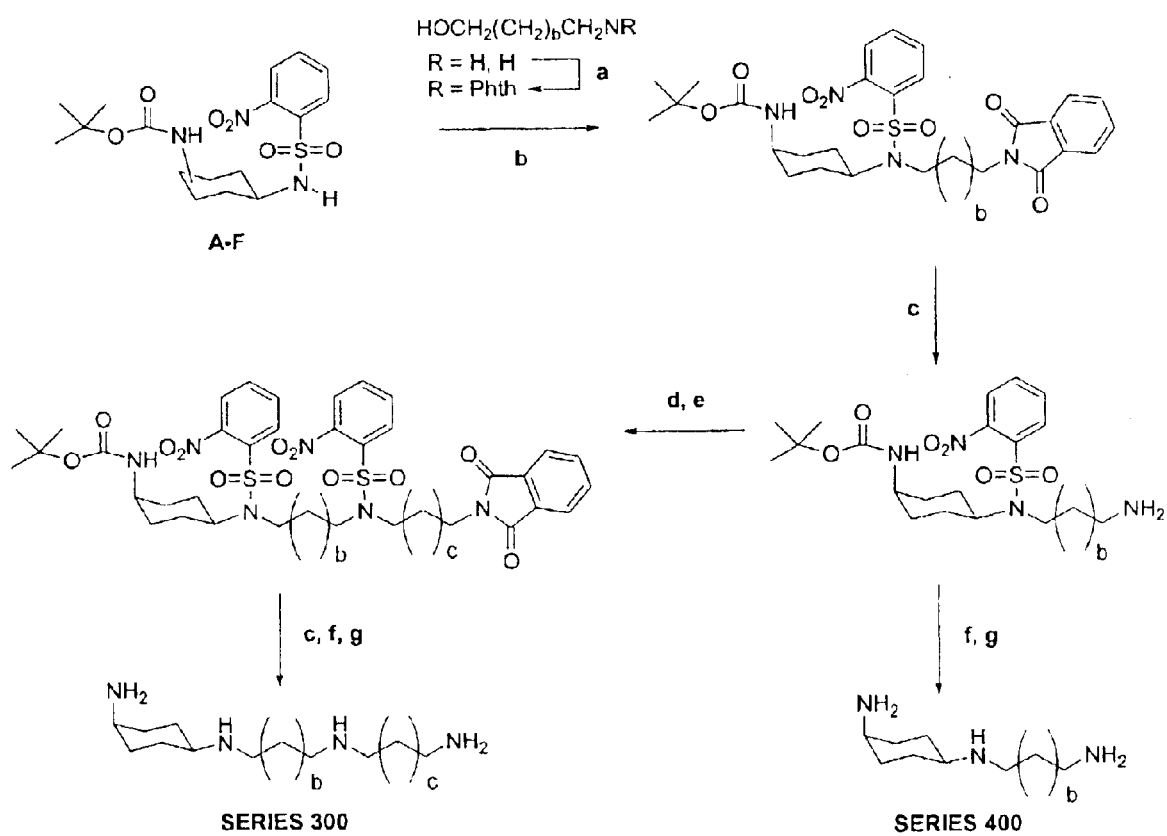
FIG. 4 shows the reaction scheme for the synthesis of "amino-walk" analogs. Reagents and conditions: Use of intermediate A is shown as an example in this route a) Phthalic anhydride, EtOH, reflux; b) $HOCH_2(CH_2)_b$ $CH_2NPhth$, $Ph_3P$, DIAD, THF, b=0 to 12; c) $NH_2NH_2$, EtOH, reflux; d) $HOCH_2(CH_2)_c CH_2NPhth$, $Ph_3P$, DIAD, THF, c=0 to 12; e) 2-nitrobenzenesulfonyl chloride, $CH_2Cl_2$, $Et_3N$; f) $HSCH_2CH_2OH$, DBU, DMF; g) 3N HCl in MeOH.

The series 300 and 400 compounds are exemplary of compounds of the present invention wherein the distance between the nitrogen atoms in the linear portion of the molecule is varied ("nitrogen-scan" or "amino-walk" analogs). Modification of the distance between the four nitrogen atoms, and thus the number of methylene units between them, is carried out by a variation on the synthetic scheme shown in FIG. 2. This modified route is shown in FIG. 4. The N-phthalimido protected amino alcohols were produced via standard conditions by refluxing the amino alcohols overnight with phthalic anhydride in ethanol. The resulting set of precursors was utilized in the route shown to give the analogs described in FIG. 5. Variations in the geometric and stereochemical arrangement of the diamine groups of the cyclohexane portion of the molecule are also envisioned via the use of the intermediates A-F shown in FIG. 2, as precursors in the scheme in FIG. 4.

Additional analogs bearing various branched or substituted functionalities can be readily envisioned. These modified analogs are tailored to possess features that increase their usefulness in biological systems. As an example, the addition of a methyl group to the carbon atom next to a nitrogen atom, especially at an aminopropyl portion, greatly reduces its ability to be metabolized by a variety of polyamine and amino oxidase enzymes. An analog of the preferred compounds addressing this modification is shown in FIG. 6.

Figure 7:
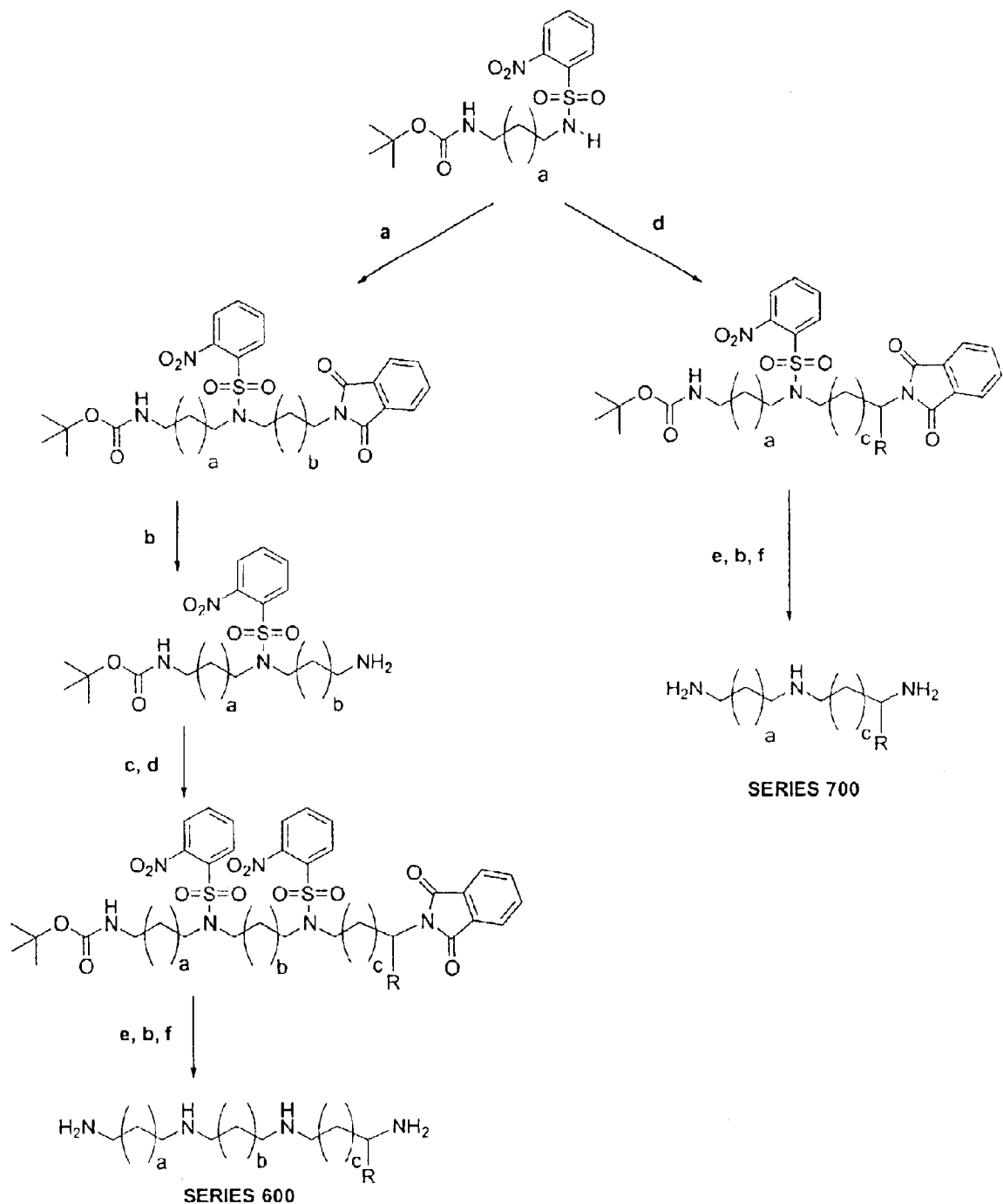
FIG. 7 shows the reaction scheme for the synthesis of series 600 and series 700 (truncated) molecules. Reagents and conditions: a) $HOCH_2(CH_2)_b CH_2NPhth$, $Ph_3P$, DIAD, THF, b=0 to 12; b) $NH_2NH_2$, EtOH, reflux; c) 2-nitrobenzenesulfonyl chloride, $CH_2Cl_2$, $Et_3N$; d) $HOCH_2(CH_2)_c CHRNPhth$, $Ph_3P$, DIAD, THF, c=0 to 12; e) $HSCH_2CH_2OH$, DBU, DMF; f) 3N HCl in MeOH.

A variety of aromatic substituted amino alcohol precursor molecules were utilized in the scheme shown in FIG. 7 to provide bioactive compounds having the naphthylene ring moiety processed by MQT 600.

Figure 8:
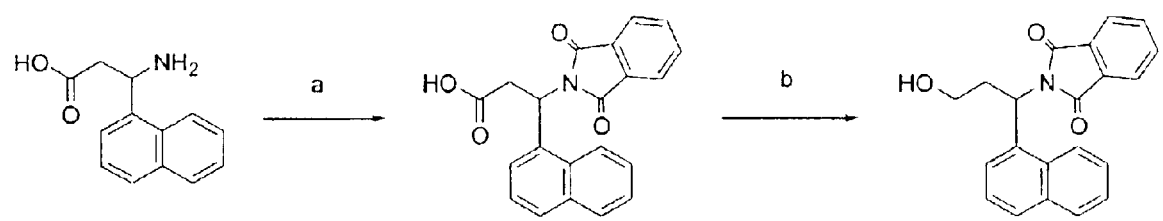
FIG. 8 shows the reaction scheme for the synthesis of aromatic substituted amino alcohol precursor molecules. Reagents and conditions: a) methyl 2-((succinimidooxy)

The aromatic substituted amino alcohol precursors were produced via the route shown in FIG. 8. Use of a new and efficient reagent enabled the N-phthaloylation of a variety of amino acid precursors (Casimir J. R., et. al. *J. Org. Chem.* 2002, 67, 3764–3768). The resulting N-phthalimide protected α and β-amino acids were then converted to their isobutyl mixed anhydrides and reduced in situ with $NaBH_4$ (Rodriquez, et. al. *Tetrahedron Lett.* 1991, 32, 923–926). These protected amino alcohols were used in the FIG. 7 route. FIG. 9 shows examples of the molecules produced in the route shown in FIG. 7 (SERIES 600 analogs). FIG. 10 shows examples of truncated molecules also produced by the route shown in FIG. 7 (SERIES 700 analogs). Several of these examples also incorporate analogs produced by changing the position of the amino groups along the polyamine backbone (the "amino-walk" analogs). Variations in the number of methylene (—$CH_2$—) groups between the amino functions not only influence the affinity for the biological target but also have a dramatic effect on the physical properties of the drug molecule. An example of a property affected includes the hydrophobic nature of the molecule. This will greatly influence the molecule's ability to penetrate biological membranes to ultimately interact with its biological target. It will also greatly impact the molecule's route of administration in the clinical setting. The most desirable features can be tailored into the molecule by adjusting the structure in a controlled and thoughtful manner once aware of the present disclosure. A field of pharmaceutical development called ADME (absorption, distribution, metabolism and elimination) has evolved to address these features of drug characteristics.

A variety of molecules can be envisioned that combine the optimized functionalities in the described series. Examples of combination molecules are shown in FIG. 11, SERIES 800.

A variety of compounds described in this invention can exist in alternate stereochemical forms and various chemical methodologies exist for the separation of one enantiomeric form from the other. As examples, MQT 600 can be separated into its enantiomeric components via one of three different methods. The first and most straightforward method would be the chromatographic or crystallographic resolution of the mixture. These methods are well established in the field and give the advantage that the two isomers can be obtained in pure form for testing. On the other hand, resolution via these methods by theory reduces the yield of the isomer of interest to <50% at best. Also, resolution by these methods still requires determination of the absolute stereochemical assignment of the individual isomers. For these reasons it is sometimes better to produce the stereoisomers in their pure form through synthesis from stereochemically pure precursors whereby the absolute form has been defined.

A second approach to synthesize the required stereoisomeric pair of MQT 600 isomers would entail an enzymatic resolution step. FIG. 12 shows a route by which a racemic mixture of β-aminoacid esters is produced via a Radionow reaction (Rodionow, W. M., et. al. *J. Am. Chem. Soc.* 1929, 51, 841–847) followed by acid-catalyzed esterification. This mixture is then treated with the esterase enzyme Amano PS that has been shown to selectively hydrolyze the (S)-isomer ester (Faulconbridge, S. J. et. al. *Tetrahedron Lett,* 2000, 41, 2679–2681). The resulting resolved ester/acid forms can be converted into the desired MQT 600 R- and S-isomers using the routes shown in this application.

Alternatively, the stereo-pure components of MQT 600 can be obtained by purchasing their stereo-defined forms and using them in the synthetic routes outlined in this application. The R- or S-enantiopure β-amino acids 1-naphthyleneglycine in their FMOC protected forms are available from BaChem AG (Switzerland). These can be homologated via an Arndt-Eistert reaction to give the FMOC-β-amino acids (Guichard, G. et. al. *Helv. Chim. Acta* 1998, 81, 187) shown in FIG. 13. These isomers can then be transformed to precursors used in the ultimate production of the isomeric forms of MQT 600 by methodology outlined in this application.

A summary of the different analogs envisioned by this invention is shown in FIG. 14.

The following non-limiting examples are presented to further illustrate an understanding of the present invention.

EXAMPLE 1

Synthesis of MQT 100

All chemical reagents and starting materials were of the highest grade available and were used without further purification. Thin-layer chromatography analysis of crude reaction products and column chromatography was performed using Merck $F_{254}$ silica gel plates and Baker 40 μm flash chromatography packing, respectively.

Trans-N-Boc-4-aminocyclohexanol—A 1.52 g (10 mmol) portion of trans-4-aminocyclohexanol hydrochloride was dissolved in 10 mL of 10% aqueous sodium carbonate and 5 mL THF and stirred at room temp. A solution of $Boc_2O$ in 15 mL THF was added and the solution stirred for 18 hours at room temp. The resulting solution was concentrated in vacuo and then partitioned between 50 mL $H_2O$ and 50 mL EtOAc. The aqueous layer was once more extracted with EtOAc and the combined organic extracts were washed with 1N HCl and brine. The organic extract was dried over $MgSO_4$ and evaporated in vacuo to give 2.02 g of a white solid. (94%). $R_f$ 0.26 (1:1 Hexane:EtOAc). This material was used directly in the next step without purification.

Trans-N-Boc-4-amino-1-phthalimido-cyclohexane—A solution of 1.5 g (7.0 mmol) of trans-N-Boc-4-aminocylcohexanol, 1.15 g (7.8 mmol) of phthalimide and 2.0 g (7.6 mmol) of $Ph_3P$ dissolved in 50 mL anhydrous THF was stirred at 0° C. under argon. A neat aliquiot of DIAD (1.67 mL, 8.5 mmol) was then added dropwise. The yellow solution was stirred for 18 hours at 25° C. at which time it was concentrated in vacuo. The product was purified by silica gel chromatography eluting first with 8:2 Hexane/EtOAc, then with 1:1 Hexane/EtOAc. A yield of 500 mg of clear oil (21%) was obtained following evaporation of product fractions as determined by TLC with ninhydrin detection ($R_f$ 0.68 (1:1 Hexane:EtOAc)).

$N^4$-Boc-$N^1$-Nbs—trans-1,4-diaminocyclohexane—A solution of 500 mg (1.5 mmol) of trans-N-Boc-4-amino-1-phthalimido-cyclohexane in 20 mL EtOH was treated with 151 μl of hydrazine hydrate. The resulting solution was stirred at room temp for 18 hours at which time the precipitate that had formed was filtered off. The filtrate was evaporated to dryness to give a total of 422 mg of the mono-Boc-1,4-diamino intermediate. This compound was then dissolved in 15 mL $CH_2Cl_2$ and 554 mg (2.5 mmol) 2-nitrobenzenesulfonyl chloride was added and the resulting solution was stirred under argon at 0° C. A portion of 348 μL of triethylamine (2.5 mmol) was then added and the solution was stirred at 25° C. for 2 hours. The reaction was then poured into aqueous 0.1N HCl and then immediately extracted with 3×50 mL portions of $CH_2Cl_2$. The combined organic extracts were washed with brine, dried over $MgSO_4$ and then evaporated to dryness. The resulting crude white solid was purified on silica gel eluting with 6:4 Hexane/EtOAc to give 415 mg (53% yield) of clear oil product ($R_f$ 0.40 (1:1 Hexane/EtOAc)).

$N^1$-Boc-$N^4$-Nbs-$N^4$-(3-propyl-1-phthalimide)-trans-1,4-diaminocyclohexane—A solution of 310 mg (0.78 mmol) of $N^4$-Boc-$N^1$-Nbs—trans-1,4-diaminocyclohexane was dissolved in 20 mL of 1:3 $CH_2Cl_2$/benzene together with 254 mg (0.97 mmol) of $Ph_3P$ and 127 mg (0.62 mmol) of N-(3-hydroxypropyl)phthalimide. The resulting solution was stirred at 25° C. under argon. To this solution was added 191 μL (0.97 mmol) of a 40% solution of DIAD in toluene dropwise. After addition was complete, stirring was continued for an additional 18 hours. The solution was evaporated to dryness and the crude oil purified on silica gel eluting first with 8:2 Hexane/EtOAc then with 1:1 Hexane/EtOAc to give a total of 322 mg (89%) of product as a clear oil ($R_f$ 0.35 (1:1 Hexane/EtOAc)).

$N^1$-Boc-$N^4$-Nbs-$N^{-4}$-(3-propyl-1-Nbs-amino)-trans-1,4-diaminocyclohexane—To a solution of 322 mg (0.55 mmol) of $N^1$-Boc-$N^4$-Nbs-$N^4$-(3-propyl-1-phthalimide)-trans-1,4-diaminocyclohexane in 10 mL of absolute EtOH was added 50 μL of neat hydrazine hydrate. The solution was stirred at room temp for 18 hours at which time the white precipitate was filtered off. Following TLC analysis of the filtrate to show no starting material remained, the solvent was evaporated to give 150 mg of white solid. This was taken immediately to next step by dissolving in 10 mL $CH_2Cl_2$ together with 93 mg (0.42 mmol) of 2-nitrobenzenesulfonyl chloride and stirring under argon at 0° C. A 59 μL (0.42 mmol) portion of dry triethylamine was then added and the solution was allowed to warm to 25° C. and stirred for an additional 18 hours. The solution was then poured into aqueous 0.1N HCl and immediately extracted 3×25 mL $CH_2Cl_2$. The combined organic extracts were washed with brine, dried over $MgSO_4$ and evaporated to dryness. The crude white solid was purified on silica gel eluting with 1:1 Hexane/EtOAc to give 142 mg (40% yield) of product as a pale yellow oil ($R_f$ 0.50 (48:48:4 Hexane/EtOAc/MeOH)).

$N^1$-Boc-$N^4$-Nbs-$N^4$-(3-propyl-1-Nbs-amino-1-(6-hexanyl-1-Boc-amino))-trans-1,4-diaminocyclohexane To a solution of 56 mg (0.087 mmol) of $N^1$-Boc-$N^4$-Nbs-$N^4$-(3-propyl-1-Nbs-amino)-trans-1,4-diaminocyclohexane dissolved in 3.0 mL of 1:3 $CH_2Cl_2$/benzene together with 30 mg (0.11 mmol) of $Ph_3P$ and 17 mg (0.080 mmol) of $N^6$-Boc-aminohexanol at 25° C. under argon was added 22 μL (0.11 mmol) of a 40% solution of DIAD in toluene. After addition was complete the reaction was stirred for an additional 18 hrs. The solution was evaporated to dryness and the crude oil was then purified on silica gel, eluting first with 8:2 Hexane/EtOAc, then with 1:1 Hexane/EtOAc, and finally with 48:48:4 Hexane/EtOAc/MeOH to give 53 mg (79%) of product as a clear oil ($R_f$ 0.30 (48:48:4 Hexane/EtOAc/MeOH)).

MQT 100—To a solution of 53 mg (0.063 mmol) of $N^1$-Boc-$N^4$-Nbs-N-(3-propyl-1-Nbs-amino-1-(6-hexanyl-1-Boc-amino))-trans-1,4-diaminocyclohexane in 2 mL of THF was added 250 μL of DBU together with 50 μL of 2-mercaptoethanol. The resulting solution was stirred at 25° C. for 18 hours and then evaporated under a stream of argon. The resulting product was purified on silica gel eluting first with 90:10 $CHCl_3$/MeOH then with 85:14:1 $CHCl_3$/MeOH/$NH_4OH$ and finally with 80:18:2 $CHCl_3$/MeOH/$NH_4OH$ to give 25 mg of the di-Boc-intermediate ($R_f$ 0.26, 80:18:2 $CHCl_3$/MeOH/$NH_4OH$). This product was then dissolved in 2 mL of 3N HCl in MeOH and stirred at 25° C. for 18 hours. The solution was evaporated to dryness, redissolved in a small volume of water and then evaporated to dryness again to give 12 mg (46%) of the HCl salt of MQT 100 as a white solid ($R_f$ 0.16 (1:1 $CH_3CN$/$NH_4OH$)).

EXAMPLE 2

Cell Culture and Reagents

The RAW264.7 cell line was obtained from ATCC (Manassas, Va.) and cultured in the recommended media, serum, and $CO_2$ concentration. Medias were obtained from Mediatech, Inc. (Herndon, Wash.) and serums from Gibco BRL (Gaithersburg, Md.). 50 U/mL penicillin, 50 mg/mL streptomycin and 2 mM L-glutamine (all from BioWhittaker, Walkersville, Md.) were included in all cultures. When cells were cultured with compounds, 1 mM aminoguanidine (AG; Sigma) was included to inhibit serum amine oxidase activity.

EXAMPLE 3

RAW264.7 Growth Inhibition Assay

Compounds were screened for cell growth inhibition by exposing RAW264.7 mouse macrophages to a range of compound concentrations up to 100 $\mu$M for 3 days. On the fourth day, MTS/PMS dye (Cell Titer 96 Aqueous Non-Radioactive Cell Proliferation Assay: Promega, Madison, Wis., USA) solution was added and the $OD_{490}$ was measured. The percent inhibition of growth compared to untreated control was ascertained and the $IC_{50}$ (concentration at which 50% of cell growth was inhibited) was computed. The numbers shown are representative of 3 independent experiments (FIG. 15).

EXAMPLE 4

TNFα Inhibition

For TNFα inhibition experiments, RAW264.7 mouse macrophages were exposed to a range of concentrations of compound for 3 days. On the fourth day, an immunostimulant, LPS(Sigma, St. Louis, Mo., USA), was added to the cell medium for four hours to induce production of TNFα, followed by harvesting of the extracellular medium. TNFα levels in the supernatant were analyzed by ELISA (R&D Systems and Endogen). The percent TNFα inhibition compared to LPS-only treated control was ascertained and the $EC_{50}$ (concentration at which 50% of TNFα secretion was inhibited) was computed. Results are the average±stdev of at least 3 independent experiments (FIG. 15).

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The compounds of this invention can be administered by any conventional method available for use in conjunction with pharmaceuticals, either as individual therapeutic agents or in a combination of therapeutic agents.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams (mg) per kilogram (kg) of body weight, with the preferred dose being 0.1 to about 30 mg/kg.

Dosage forms (compositions suitable for administration) contain from about 1 mg to about 500 mg of active ingredient per unit. In these pharmaceutical compositions, the active ingredient will ordinarily be present in an amount of about 0.5–95% weight based on the total weight of the composition.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation of a drug powder mist. Other dosage forms are potentially possible such as administration transdermally, via patch mechanism or ointment. The active ingredient can be administered employing a sustained or delayed release delivery system or an immediate release delivery system.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, Eds., 238–250 (1982) and *ASHP Handbook on Injectable Drugs*, Toissel, 4th ed., 622–630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouth washes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable pharmaceutical carriers are described in Remington's Pharmaceutical Sciences, Mack Publishing Company, a standard reference text in this field.

The dose administered to an animal, particularly a human, in the context of the present invention should be sufficient to effect a therapeutic response in the animal over a reasonable time frame. One skilled in the art will recognize that dosage will depend upon a variety of factors including a condition of the animal, the body weight of the animal, as well as the condition being treated.

A suitable dose is that which will result in a concentration of the active agent in a patient which is known to effect the desired response.

The size of the dose also will be determined by the route, timing and frequency of administration as well as the existence, nature, and extent of any adverse side effects that might accompany the administration of the compound and the desired physiological effect.

Useful pharmaceutical dosage forms for administration of the compounds according to the present invention can be illustrated as follows:

Hard Shell Capsules

A large number of unit capsules are prepared by filling standard two-piece hard gelatine capsules each with 100 mg of powdered active ingredient, 150 mg of lactose, 50 mg of cellulose and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets

A large number of tablets are prepared by conventional procedures so that the dosage unit is 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability or delay absorption.

Immediate Release Tablets/Capsules

These are solid oral dosage forms made by conventional and novel processes. These units are taken orally without water for immediate dissolution and delivery of the medication. The active ingredient is mixed in a liquid containing ingredients such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Moreover, the compounds of the present invention can be administered in the form of nose drops, or metered dose and a nasal or buccal inhaler. The drug is delivered from a nasal solution as a fine mist or from a powder as an aerosol.

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:

1. A compound having the structure as shown below:

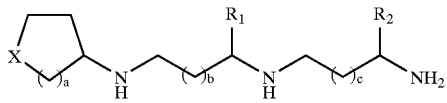

wherein, a, b and c may be the same or different and are integers from 0 to 12, X equals NH or $CHNH_2$, $R_1$ and $R_2$ can be the same or different and equal to a hydrogen or a straight or branched $C_1$ to $C_{20}$ saturated or unsaturated aliphatic; aliphatic amine; an alicyclic; single or multi-ring aromatic; a single or multi-ring aromatic heterocycle; a single or multi-ring saturated heterocycle and the halogenated forms thereof; and pharmaceutically acceptable salts thereof and prodrugs thereof.

2. The compound according to claim 1 wherein said structure has the formula:

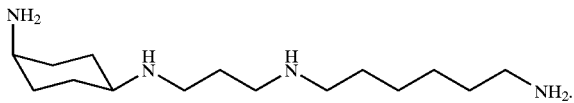

3. A compound having the structure as shown below:

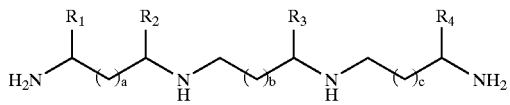

wherein, a, b and c may be the same or different and are integers from 0 to 12; $R_1$, $R_2$ and $R_3$ can be the same or different and equal to a hydrogen or a straight or branched $C_1$ to $C_{20}$ saturated or unsaturated aliphatic; aliphatic amine: an alicyclic; single or multi-ring aromatic; a single or multi-ring aromatic heterocycle; a single or multi-ring saturated heterocycle and the halogenated forms thereof; and $R_4$ is a single or multi-ring aromatic; and the halogenated forms thereof; and pharmaceutically acceptable salts thereof and prodrugs thereof.

4. A compound having the formula:

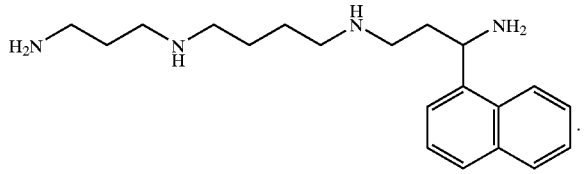

5. A pharmaceutical composition useful for treating a disease or condition which modulates the production, release or activity of cytokines of inflammatory cells comprising a compound according to claim 1 and a pharmaceutically acceptable excipient, diluent or vehicle if desirable.

6. A pharmaceutical composition useful for treating a disease or condition which modulates the production, release or activity of cytokines of inflammatory cells comprising a compound according to claim 2 and a pharmaceutically acceptable excipient, diluent or vehicle if desirable.

7. A pharmaceutical composition useful for treating a disease or condition which modulates the production, release or activity of cytokines of inflammatory cells comprising a compound according to claim 3 and a pharmaceutically acceptable excipient, diluent or vehicle if desirable.

8. A pharmaceutical composition useful for treating a disease or condition which modulates the production, release or activity of cytokines of inflammatory cells comprising a compound according to claim 4 and a pharmaceutically acceptable excipient, diluent or vehicle if desirable.

9. A pharmaceutical composition, according to any one of claims 5 to 8, useful for treating a disease or condition in which the inhibition of the expression or activity of any or all inflammatory cytokines is desirable.

10. The composition of any one of claim 5–8 wherein said excipient, diluent or vehicle is for topical or intra-aural administration.

11. The composition of any one of claims 5–8 formulated for intravenous, subcutaneous, intramuscular, intracranial, intraperitoneal, topical, transdermal, intravaginal, intranasal, intrabronchial, intracranial, intraocular, lntraaural, rectal, or parenteral administration.

12. A method of treating one or more conditions associated with unwanted or undesirable presence or activity of inflammatory cytokines comprising administration of a compound according to any one of claims 1–4.

13. The method of claim 12 wherein said administration is systemic.

14. The method of claim 12 wherein said administration is oral.

15. The method of claim 12 wherein said administration is via time-release vehicle.

16. A method according to claim 12 wherein said condition is selected from the group consisting of chronic or acute inflammation, inflammatory bowel disease, ulcerative colitis, irritable bowel syndrome, autoimmune diseases, rheumatoid arthritis, systemic lupus erythematosus, cutaneous forms of lupus, diabetes, multiple sclerosis, psoriasis, spondyloarthropathies (SpA), synovitis, psoriatic arthritis and subclinical gut inflammation and infectious diseases proliferative diseases and disorders.

17. The pharmaceutical composition, according to 9 wherein said inflammatory cytokines are selected from the group consisting of TNFα, interleukin-1β, interleukin-2, interleukin-6, interleukin-8, interleukin-12, interleukin-18, nitric oxide, granulocyte macrophage-colony stimulating factor, granulocyte-colony-stimulating factor, macrophage-colony-stimulating factor, and interferon γ.

18. The method according to claim 16 wherein said infectious diseases are selected from the group consisting of sepsis, septic shock, endotoxic shock, HIV, cytomegalovirus, herpes simplex virus, and influenza virus and wherein said proliferative diseases is cancer.

* * * * *